US009439603B2

(12) United States Patent
Takei (10) Patent No.: US 9,439,603 B2
(45) Date of Patent: Sep. 13, 2016

(54) MAGNETIC RESONANCE IMAGING APPARATUS AND METHOD (75) Inventor: Naoyuki Takei, Tokyo (JP)

(73) Assignee: General Electric Company, Schenectady, NY (US)

(*) Notice: Subject to any disclaimer, the term of this patent is extended or adjusted under 35 U.S.C. 154(b) by 824 days.

(21) Appl. No.: 13/338,416

(22) Filed: Dec. 28, 2011

(65) Prior Publication Data

US 2012/0161765 A1  Jun. 28, 2012
US 2013/0027036 A9  Jan. 31, 2013

(30) Foreign Application Priority Data

Dec. 28, 2010  (JP) .................................. 2010-292725

(51) Int. Cl.
G01R 33/54 (2006.01)
G01R 33/34 (2006.01)
A61B 5/00 (2006.01)
A61B 5/055 (2006.01)
G01R 33/563 (2006.01)
G01R 33/567 (2006.01)
A61B 5/0456 (2006.01)
A61B 5/113 (2006.01)
G01R 33/56 (2006.01)

(52) U.S. Cl.
CPC ............ *A61B 5/7285* (2013.01); *A61B 5/055* (2013.01); *G01R 33/5635* (2013.01); *G01R 33/5673* (2013.01); *A61B 5/0456* (2013.01); *A61B 5/1135* (2013.01); *G01R 33/5602* (2013.01); *G01R 33/5607* (2013.01)

(58) Field of Classification Search
CPC .......... G01R 33/5635; G01R 33/5673; G01R 33/5602; G01R 33/5607; A61B 5/055; A61B 5/7285; A61B 5/0456; A61B 5/1135

USPC .......................... 324/307, 309; 600/410–413
See application file for complete search history.

(56) References Cited

U.S. PATENT DOCUMENTS

| 4,777,959 A * | 10/1988 | Wallach et al. ................ 600/490 |
| 7,538,549 B2 | 5/2009 | Takei |
| 2008/0211497 A1* | 9/2008 | Iwadate et al. ............... 324/307 |
| 2008/0242973 A1* | 10/2008 | Warmuth ....................... 600/413 |
| 2009/0018433 A1* | 1/2009 | Kassai et al. ................. 600/413 |
| 2009/0171186 A1 | 7/2009 | Takei |
| 2009/0221905 A1 | 9/2009 | Takei |
| 2009/0245607 A1* | 10/2009 | Sugiura ......................... 382/131 |
| 2009/0270719 A1* | 10/2009 | Miyoshi ........................ 600/413 |
| 2010/0045290 A1* | 2/2010 | Miyoshi ........................ 324/309 |
| 2010/0198046 A1 | 8/2010 | Takei |
| 2010/0219830 A1 | 9/2010 | Takei |
| 2010/0249574 A1* | 9/2010 | Miyazaki ...................... 600/413 |
| 2010/0264922 A1 | 10/2010 | Xu |
| 2010/0312098 A1* | 12/2010 | Miyazaki ...................... 600/413 |

FOREIGN PATENT DOCUMENTS

| CN | 101455565 A | 6/2009 |
| CN | 101564297 A | 10/2009 |
| JP | 2008148806 | 7/2008 |
| JP | 2010082436 | 4/2010 |
| JP | 2010194243 | 9/2010 |
| JP | 2010220859 | 10/2010 |

* cited by examiner

Primary Examiner — Melissa Koval
Assistant Examiner — Rishi Patel (57) ABSTRACT

A magnetic resonance imaging apparatus configured to carry out a pulse sequence in synchronization with a biosignal is provided. The pulse sequence includes an RF pulse, and a data acquisition sequence for acquiring data when a wait time has passed after the RF pulse, wherein the wait time has a variable value that can be varied based on the biosignal.

10 Claims, 9 Drawing Sheets

MAGNETIC RESONANCE IMAGING APPARATUS AND METHOD

CROSS REFERENCE TO RELATED APPLICATIONS

This application claims the benefit of Japanese Patent Application No. 2010-292725 filed Dec. 28, 2010, which is hereby incorporated by reference in its entirety.

BACKGROUND OF THE INVENTION

The present invention relates to a magnetic resonance imaging apparatus that carries out a pulse sequence in synchronization with a biosignal.

As methods for acquiring an image of a blood flow in the abdomen of a subject, respiratory gating method and heart rate gating method are known. In the respiratory gating method, a pulse sequence is carried out in synchronization with respiration signals. In the heart rate gating method, a pulse sequence is carried out in synchronization with heart rate signals. (See, e.g., Japanese Unexamined Patent Application Publication No. 2008-148806 and Japanese Unexamined Patent Application Publication No. 2010-220859.)

In the respiratory gating method, the respiration of a subject is detected and the timing with which a pulse sequence is carried out is determined so that data can be acquired during a period for which body motion arising from respiration is small. However, if the respiration of a subject becomes irregular during scanning, data cannot be acquired during a period for which the body motion is small and the image quality may be degraded.

In the heart rate gating method, the heart rate of a subject is detected and the timing with which a pulse sequence is carried out is determined so that data can be acquired during a desired period of cardiac phase (for example, diastole). However, if the heart rate becomes irregular because of such a cause as arrhythmia during scanning, data cannot be acquired during a desired period of cardiac phase and the image quality may be similarly degraded.

Therefore, an image whose quality is not degraded so much even though the respiration or heart rate of a subject becomes irregular during scanning is desired.

SUMMARY OF THE INVENTION

A magnetic resonance imaging apparatus that carries out a pulse sequence in synchronization with a biosignal is provided.

The pulse sequence includes an RF pulse, and a data acquisition sequence for acquiring data when a wait time has passed after the RF pulse.

The wait time takes a variable value that can be varied based on the biosignal.

The start timing of a data acquisition sequence can be adjusted by providing the wait time with a variable value that can be varied based on a biosignal. Therefore, degradation in image quality can be reduced.

Further advantages will be apparent from the following description of exemplary embodiments of as illustrated in the accompanying drawings.

DETAILED DESCRIPTION OF THE INVENTION

Hereafter, exemplary embodiments will be described with reference to the drawings. However, the invention is not limited to the embodiments specifically described herein.

First Embodiment

Figure 1:
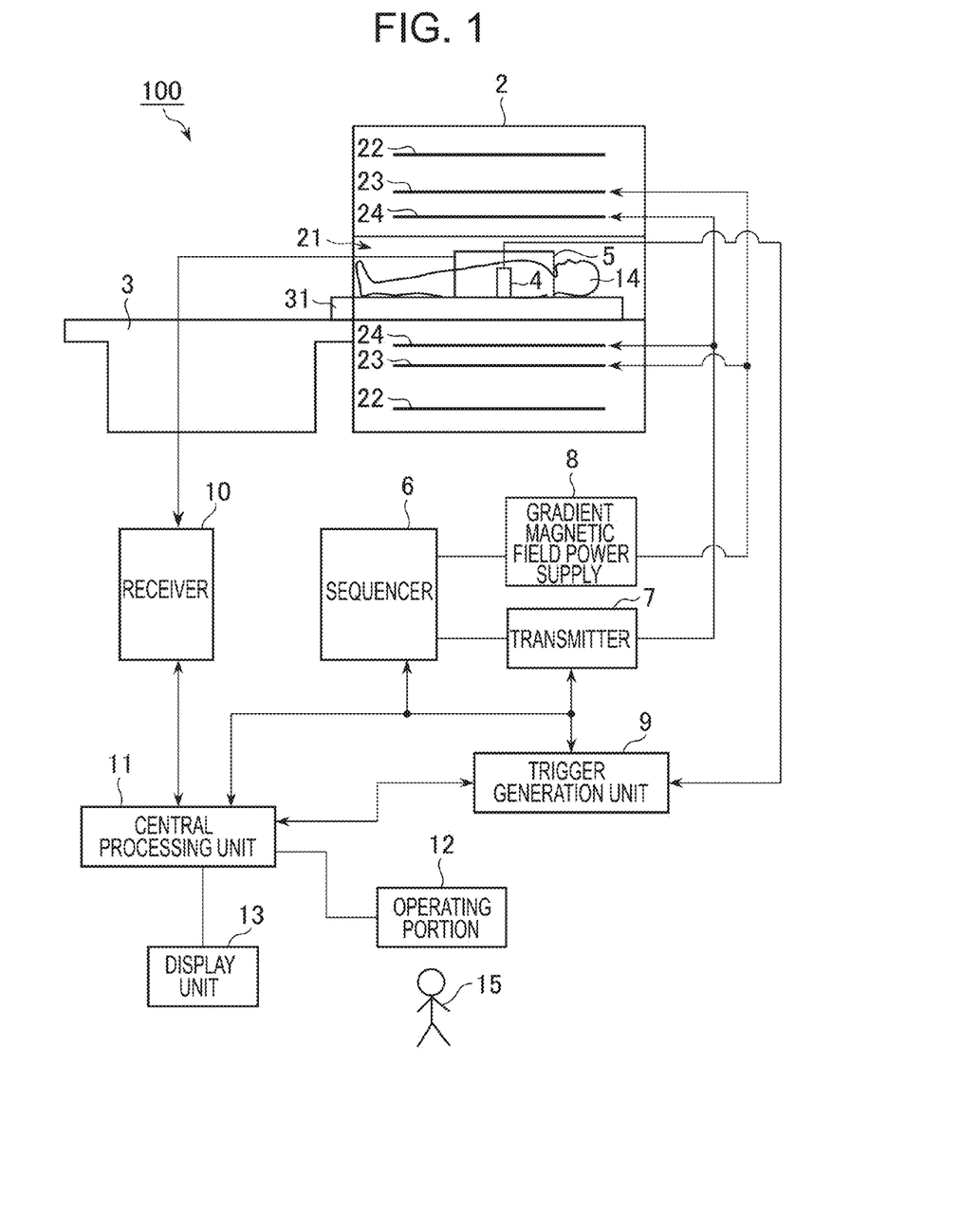
FIG. 1 is a schematic diagram of a magnetic resonance imaging apparatus in a first embodiment.

FIG. 1 is a schematic diagram of a magnetic resonance imaging apparatus in the first embodiment.

The magnetic resonance imaging ("MRI") apparatus 100 includes a magnetic field generator 2, a table 3, a bellows 4, a receiving coil 5, and the like.

The magnetic field generator 2 includes a bore 21 in which a subject 14 is placed, a superconducting coil 22, a gradient coil 23, and a transmitting coil 24. The superconducting coil 22 applies a static magnetic field B0, the gradient coil 23 applies a gradient pulse, and the transmitting coil 24 transmits an RF pulse.

The table 3 has a cradle 31 for carrying the subject 14. The subject 14 is carried into the bore 21 by the cradle 81.

The bellows 4 acquires respiration signals from the subject 14.

The receiving coil 5 is installed over the chest and abdomen of the subject 14 and receives magnetic resonance signals from the subject 14.

The MRI apparatus 100 further includes a sequencer 6, a transmitter 7, a gradient magnetic field power supply 8, a trigger generation unit 9, a receiver 10, a central processing unit 11, an operating portion 12, and a display 13.

Under the control of the central processing unit 11 and the like, the sequencer 6 sends information for acquiring an image of the subject 14 to the transmitter 7 and the gradient magnetic field power supply 8.

The transmitter 7 drives the transmitting coil 24 based on information sent from the sequencer 6.

The gradient magnetic field power supply 8 drives the gradient coil 23 based on information sent from the sequencer 6.

The trigger generation unit 9 generates a respiration synchronization trigger based on a respiration signal from the bellows 4.

The receiver 10 carries out various processing on a magnetic resonance signal received at the receiving coil 5 and transmits it to the central processing unit 11.

The central processing unit 11 controls the operation of each part of the MRI apparatus 100 so that the various operations of the MRI apparatus 100 are performed. Examples of such operations include transmitting required information to the sequencer 6 and the display 13, reconstructing an image based on a signal received from the receiver 10, and the like.

The operating portion 12 inputs various commands to the central processing unit 11 in accordance with operation by an operator 15. The display 13 displays varied information.

An image of the subject 14 is acquired using the MRI apparatus 100 configured as mentioned above.

Figure 2A:
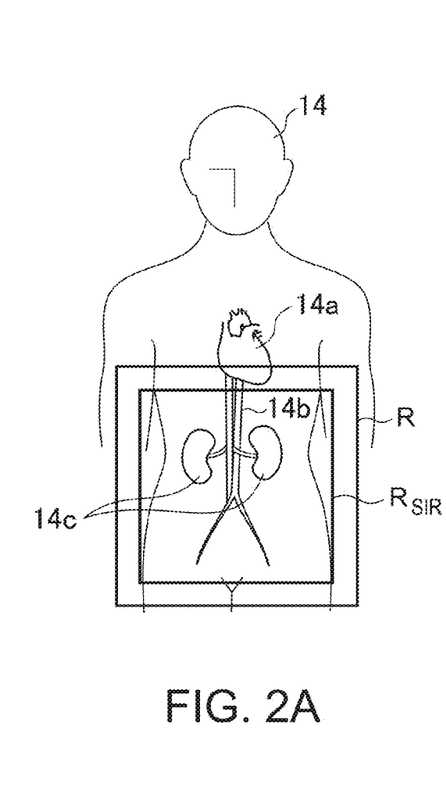
FIGS. 2A and 2B are drawings showing a case where a subject 14 is scanned.
Figure 2B:
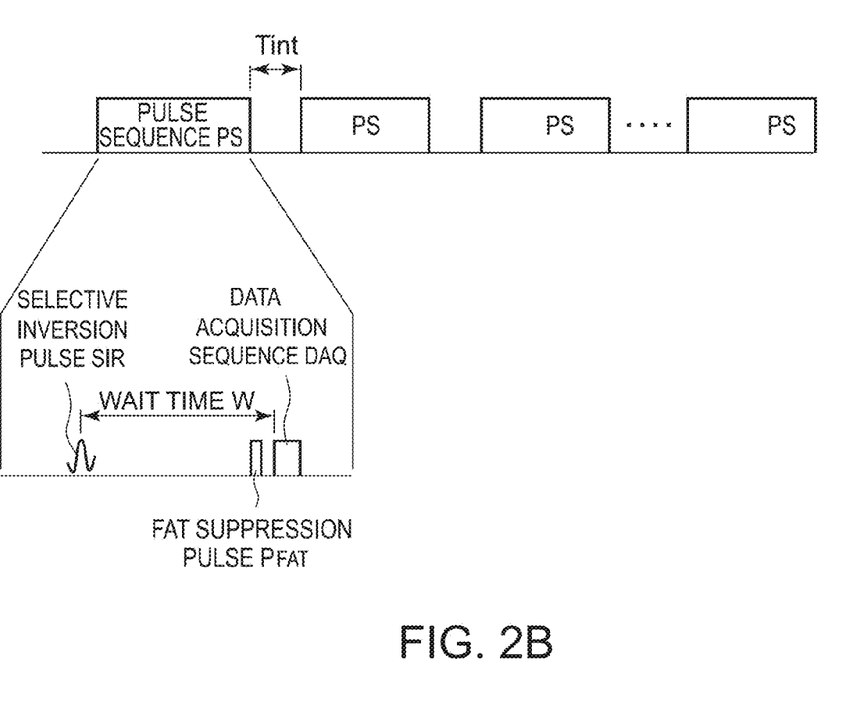

FIGS. 2A and 2B are diagrams showing a case where the subject 14 is scanned.

FIG. 2A is a diagram schematically showing an image acquisition region of the subject, and FIG. 2B is a diagram showing an example of a pulse sequence PS used when the subject 14 is scanned.

In the first embodiment, a scan for representing arterial blood 14$b$ in an image acquisition region R embracing the kidney 14$c$ is carried out utilizing the inflow effect of the arterial blood 14$b$ from the heart 14$a$. During this scan, the pulse sequence PS is repeatedly carried out as shown in FIG. 2B.

Each pulse sequence PS includes a selective inversion pulse SIR (Selective Inversion Recovery), a fat suppression pulse PFAT, and a data acquisition sequence DAQ.

The selective inversion pulse SIR is a pulse that inverts the longitudinal magnetization of the tissue (arterial blood, venous blood, fat, muscle, and the like) of an inverted region $R_{SIR}$ of the subject 14. When a wait time W (inversion time) has passed after the selective inversion pulse SIR, the data acquisition sequence DAQ for acquiring data on the image acquisition region R is carried out. Examples of the data acquisition sequence are 3D FSE (Fast Spin Echo) and FIESTA (Fast Imaging Employing Steady state Acquisition). The heart 14$a$ is located outside the inverted region $R_{SIR}$; therefore, the arterial blood in the heart 14$a$ remains with the longitudinal magnetization M=1 even though a selective inversion pulse SIR is transmitted. During the wait time W, therefore, the arterial blood 14$b$ with the longitudinal magnetization M=1 flows from the heart 14$a$ into the image acquisition region R. Therefore, an MRI image in which arterial blood is emphatically represented and background tissue (venous blood and the like) is suppressed can be obtained by carrying out the data acquisition sequence DAQ. A fat suppression pulse $P_{FAT}$ is transmitted immediately before the data acquisition sequence DAQ. Therefore, the fat signals from the image acquisition region R can be effectively suppressed. Examples of the fat suppression pulse $P_{FAT}$ are SPECIR (Spectrally Selected IR) and STIR (Short-TI IR).

In each pulse sequence PS, the wait time W has a variable value that can be varied based on a respiration signal from the subject 14. As the result of providing the wait time W with a variable value, image data in which body motion artifacts arising from respiration are sufficiently reduced can be acquired even though the respiration of the subject becomes irregular while an image of the subject is being acquired. Hereafter, description will be given to the reason for this.

Figure 3A:
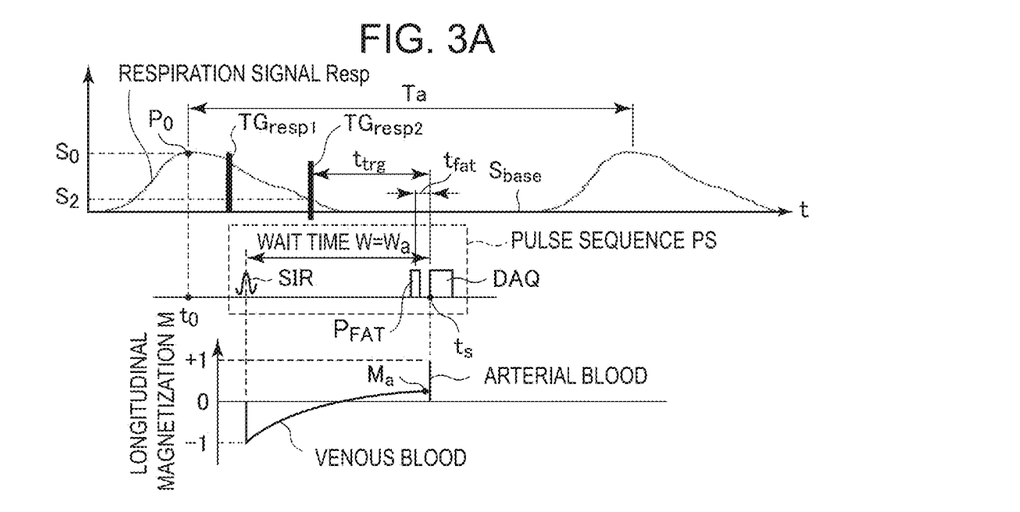
FIGS. 3A and 3B are drawings showing the relation between a respiration signal Resp and a pulse sequence PS.
Figure 3B:
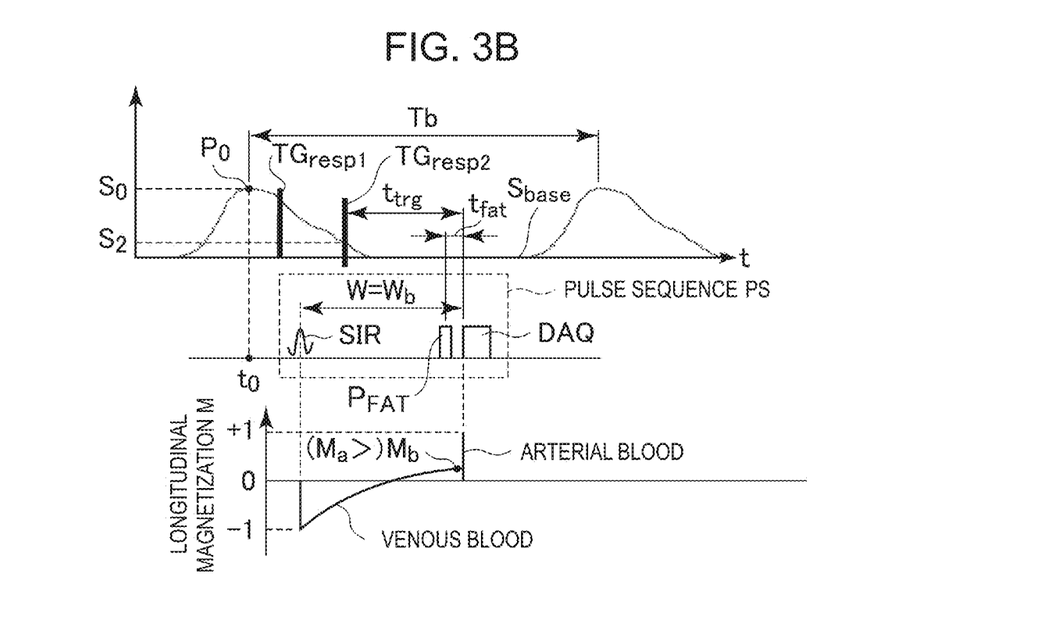

FIGS. 3A and 3B are drawings showing the relation between a respiration signal Resp and a pulse sequence PS.

FIG. 3A is a drawing showing a pulse sequence PS in the case of respiratory cycle $T_a$, and FIG. 3B is a drawing showing a pulse sequence PS in the case of respiratory cycle $T_b$ ($<T_a$).

First, FIG. 3A will be described.

The trigger generation unit 9 (Refer to FIG. 1) detects a peak of the respiration signal Resp based on the signal value of the respiration signal Resp. In FIG. 3A, the peak $P_0$ of the respiration signal Resp occurs at time $t_0$, therefore, the trigger generation unit 9 detects the peak $P_0$. When the trigger generation unit 9 detects the peak $P_0$, it generates a first respiration synchronization trigger $TG_{resp1}$ for transmitting the selective inversion pulse SIR. The first respiration synchronization trigger $TG_{resp1}$ may be generated at the position of the peak $P_0$ or may be generated temporally behind the peak $P_0$. In the first embodiment, the first respiration synchronization trigger $TG_{resp1}$ is generated temporally behind the peak $P_0$.

When the first respiration synchronization trigger $TG_{resp1}$ is generated, the selective inversion pulse SIR is transmitted in synchronization with the first respiration synchronization trigger $TG_{resp1}$. The longitudinal magnetization of tissue contained in the inverted region $R_{SIR}$ (Refer to FIG. 2A) is inverted by the selective inversion pulse SIR. In FIG. 3A, venous blood is shown as the tissue whose longitudinal magnetization is inverted by the selective inversion pulse SIR.

After transmitting the selective inversion pulse SIR, the trigger generation unit 9 generates a second respiration synchronization trigger $TG_{resp2}$ for carrying out the data acquisition sequence DAQ while the body motion of the subject 14 arising from respiration is small. The second respiration synchronization trigger $TG_{resp2}$ can be generated, for example, when the signal value of the respiration signal Resp is lowered to $S_2$. The value of the signal value $S_2$ can be represented by, for example, Expression (1) below:

$$S_2 = k(S_0 - S_{base}) \quad (1)$$

where, k is a coefficient, $S_0$ is the signal value of the peak $P_0$ of the respiration signal Resp, and $S_{base}$ is the base line of the respiration signal Resp.

The base line $S_{base}$ of the respiration signal Resp represents a signal value at the time when the body motion of the subject 14 arising from respiration is sufficiently small. The base line $S_{base}$ is calculated beforehand based on, for example, the respiration signal Resp before time $t_0$. For example, Expression (1) is converted into the following expression when the base line $S_{base}=0$:

$$S_2 = k \times S_0 \quad (2)$$

Therefore, the signal value $S_2$ can be determined by k and $S_0$. With respect to the value k, for example, k=0.1 can be taken. When k=0.1, $S_2=0.1 \times S_0$. Therefore, the second respiration synchronization trigger $TG_{resp2}$ is generated when the signal value of the respiration signal Resp is lowered by 90% from the peak value $S_0$. Therefore, the second respiration synchronization trigger $TG_{resp2}$ can be generated when the respiration signal Resp gets sufficiently close to the base line $S_{base}$.

When the second respiration synchronization trigger $TG_{resp2}$ is generated, the fat suppression pulse $P_{FAT}$ is transmitted and the data acquisition sequence DAQ is carried out. In FIG. 3A, the time interval from the second respiration synchronization trigger $TG_{resp2}$ to when the data acquisition sequence DAQ is started is indicated by symbol "$t_{trg}$", and the time interval from the fat suppression pulse $P_{FAT}$ to when the data acquisition sequence DAQ is started is indicated by symbol "$t_{fat}$."

The time interval $t_{trg}$ from the second respiration synchronization trigger $TG_{resp2}$ to when the data acquisition sequence DAQ is started is set so that the data acquisition sequence DAQ can be carried out while body motion arising from respiration is small. A fixed value determined before the subject 14 is scanned can be taken for the time interval $t_{trg}$. However, when the respiratory cycle of the subject 14 largely fluctuates during scanning, the respiratory cycle of the subject 14 may be measured periodically (for example, at intervals of more than 10 seconds to several tens of seconds) while the subject 14 is scanned, and the value of time interval $t_{trg}$ may be changed based on the latest measured respiratory cycle. The time interval $t_{fat}$ from the fat suppression pulse $P_{FAT}$ to when the data acquisition sequence DAQ is started generally has a fixed value. However, the value may be changed as required.

The longitudinal magnetization of the venous blood in the inverted region $R_{SIR}$ is inverted by the selective inversion pulse SIR but it is gradually restored during the wait time $W=W_a$. If the respiratory cycle $T_a$ is, for example, 4 seconds, the wait time $W_a$ is, for example, 1.5 seconds or so. In this case, the longitudinal magnetization of venous blood has been restored to $M_a$ at the start time $t_s$ of the data acquisition sequence DAQ as indicated by the graph of longitudinal magnetization in FIG. 3A. During the wait time $W_a$, meanwhile, arterial blood with the longitudinal magnetization M=1 flows from the heart 14a located outside the inverted region $R_{SIR}$ (Refer to FIG. 2A) into the image acquisition region R. In the image acquisition region R, therefore, the longitudinal magnetization of arterial blood is sufficiently larger than the longitudinal magnetization of venous blood at the start time $t_s$ of the data acquisition sequence DAQ. For this reason, an image in which arterial blood is emphasized more than venous blood can be obtained.

FIG. 3B shows a case where the respiratory cycle of the subject 14 transitions from $T_a$ to $T_b$ while the subject 14 is scanned. Also in FIG. 3B, the pulse sequence PS is carried out in the same manner as in FIG. 3A and accordingly, detailed description of FIG. 3B will be omitted.

As shown in FIGS. 3A and 3B, in the first embodiment, the second respiration synchronization trigger $TG_{resp2}$ is generated when after the selective inversion pulse SIR is transmitted, the respiration signal Resp gets close to the base line $S_{base}$. Therefore, if the respiratory cycle of the subject 14 changes during scanning, the generation timing of the second respiration synchronization trigger $TG_{resp2}$ is changed in accordance with this change. As a result, the value of the wait time W of the pulse sequence is also changed. As is apparent from the comparison of FIG. 3A and FIG. 3B, the wait time W of the pulse sequence PS is $W=W_a$ in FIG. 3A while the wait time W of the pulse sequence PS is changed to $W=W_b$ in FIG. 3B. Therefore, the start timing of the data acquisition sequence DAQ can be adjusted by taking a variable value for the wait time W. This makes it possible to carry out the data acquisition sequence DAQ while the body motion of the subject 14 arising from respiration is small and obtain an image with reduced body motion artifacts.

In the first embodiment, the wait time W of the pulse sequence PS varies according to variation in the respiratory cycle of the respiration signal Resp during scanning. Therefore, the degree of restoration of the longitudinal magnetization of venous blood differs. As is apparent from the comparison of FIG. 3A and FIG. 3B, the longitudinal magnetization of venous blood is restored substantially to $M=M_a$ in FIG. 3A while the longitudinal magnetization of venous blood is restored only to $M=M_b$ ($<M_a$) in FIG. 3B.

Also with respect to the background tissues (muscle, fat, and the like) other than venous blood, similarly to venous blood, the degree of restoration of longitudinal magnetization differs according to variation in the wait time W of the pulse sequence PS. Therefore, the contrast between arterial blood and background tissue may be reduced when the wait time W of the pulse sequence PS is varied. However, since the arterial blood in the image acquisition region R when the data acquisition sequence DAQ is carried out is with longitudinal magnetization M=1, it is sufficiently larger than the longitudinal magnetization of background tissue. Therefore, it is supposed that sufficient contrast can be maintained even though the wait time W of the pulse sequence PS varies. To verify this, simulation was carried out. Hereafter, description will be given to the result of this simulation.

Figure 4A:
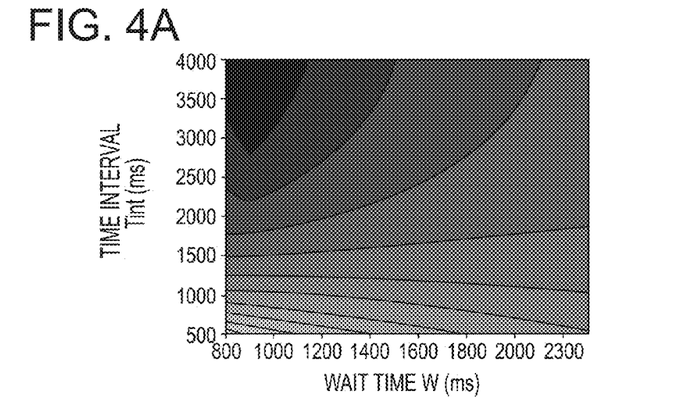
FIGS. 4A-4C are drawings showing the result of simulation.
Figure 4B:
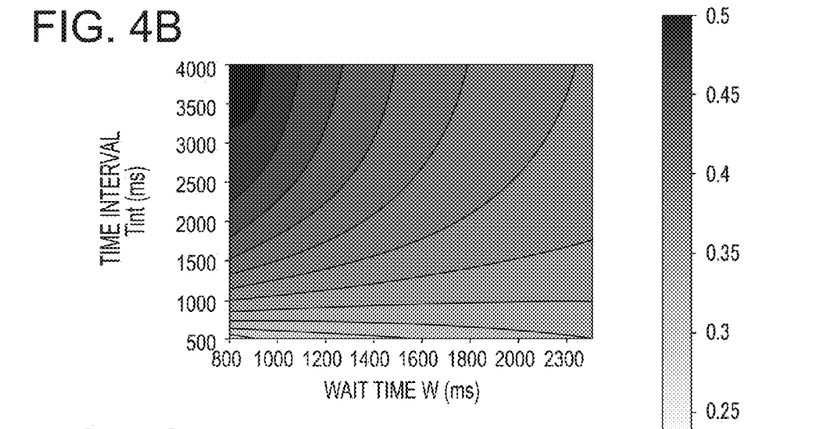
Figure 4C:
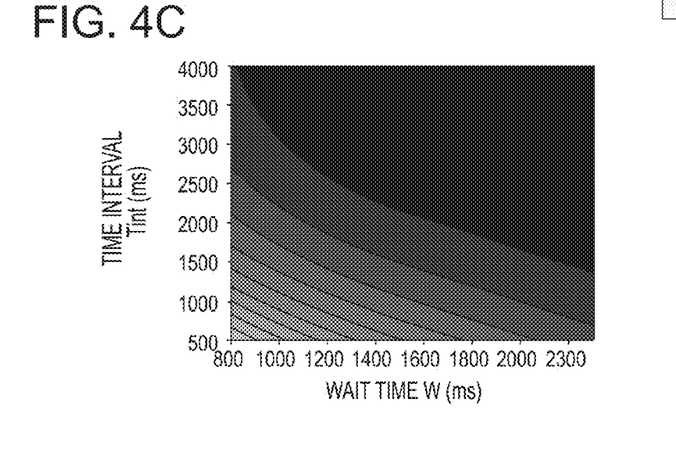

FIGS. 4A-4C are drawings showing the simulation result.

FIG. 4A is a drawing showing the contrast between arterial blood and venous blood, FIG. 4B is a drawing showing the contrast between arterial blood and muscle, and FIG. 4C is a drawing showing contrast between arterial blood and fat.

The horizontal axes of FIGS. 4A-4C represent the wait time W of the pulse sequence PS and the vertical axes represent the time interval $T_{int}$ between a pulse sequence PS and the next pulse sequence. (Refer to FIG. 2B.)

As is apparent from FIGS. 4A-4C, when the time interval $T_{int}$ is, for example, 2000 (ms), even though the wait time W fluctuates between W=1400 (ms) and 1900 (ms), the contrast is not less than 0.4 and arterial blood can be sufficiently represented. Therefore, it is guessed that variation in the wait time W of the pulse sequence PS has relatively little influence on image quality.

The pulse sequence PS includes a fat suppression pulse $P_{FAT}$ between the selective inversion pulse SIR and the data acquisition sequence DAQ. However, the fat suppression pulse $P_{FAT}$ may be removed as required or a different RF pulse may be provided in place of the fat suppression pulse $P_{FAT}$. Further, a different RF pulse may be provided in addition to the fat suppression pulse $P_{FAT}$.

The pulse sequence PS shown in FIGS. 2A and 2B includes the selective inversion pulse SIR. However, a non-selective inversion pulse may be used or an α°-RF pulse (α°≠180°) may be used in place of the selective inversion pulse SIR.

Second Embodiment

In the description of the second embodiment, a case where the heart rate gating method is used to acquire an image of a subject will be taken as an example.

Figure 5:
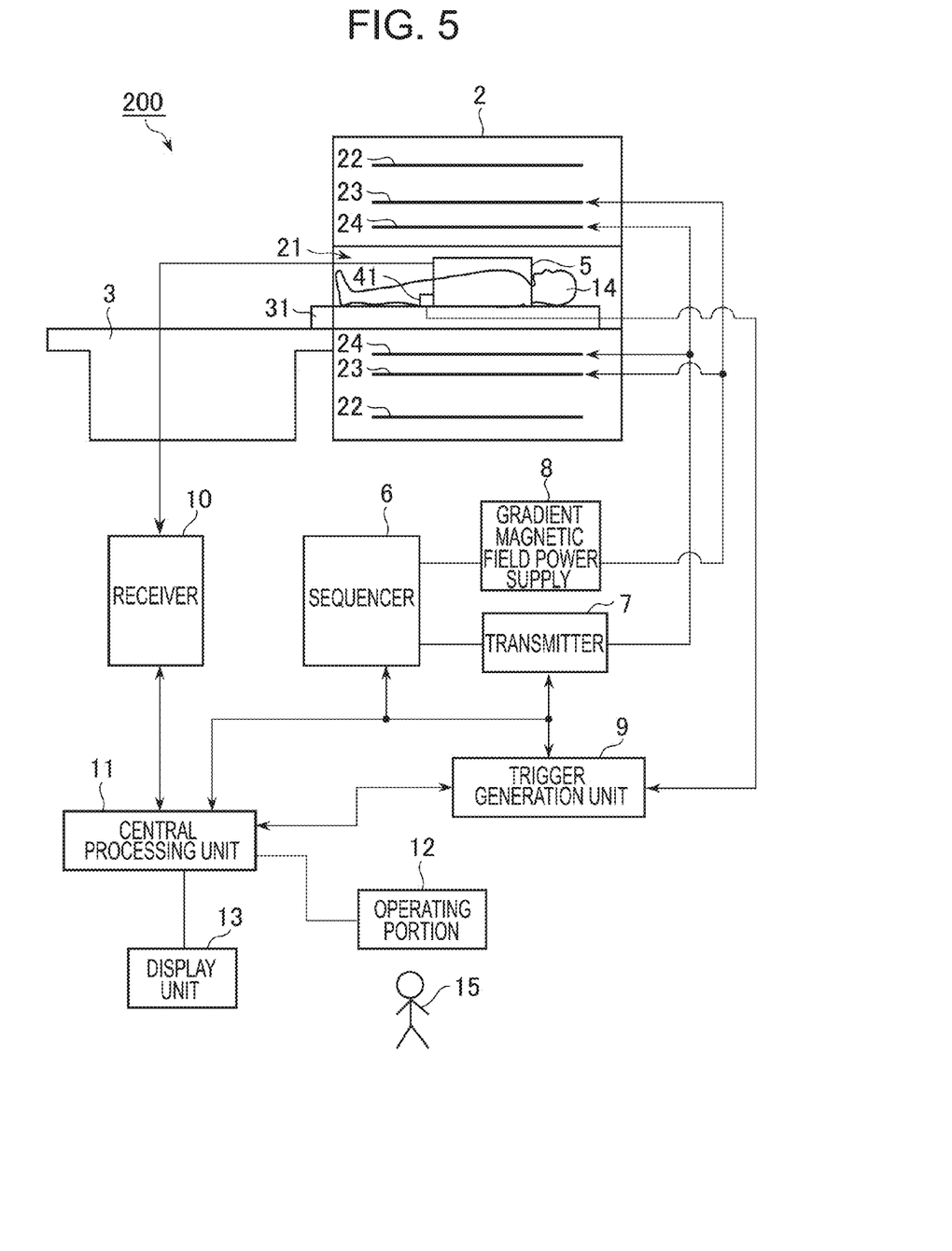
FIG. 5 is a diagram showing an MRI apparatus in a second embodiment.

FIG. 5 is a diagram showing an MRI apparatus 200 in the second embodiment.

The MRI apparatus 200 in the second embodiment is different from the MRI apparatus 100 in the first embodiment in that a heart rate sensor 41 for acquiring heart rate signals from the subject 14 is provided in place of the bellows 4. The heart rate sensor 41 is, for example, a sphygmograph sensor. The second embodiment is also different in that trigger generation unit 9 generates a heart rate synchronization trigger based on a heart rate signal from the heart rate sensor 41.

The other configuration elements are the same as those of the MRI apparatus 100 in the first embodiment and the description thereof will be omitted.

The MRI apparatus 200 in the second embodiment is configured as mentioned above. Description will be given to a method for scanning the subject 14 in the second embodiment. The image acquisition region R and the pulse sequence PS in the second embodiment are as shown in FIGS. 2A and 2B similarly to the first embodiment.

Figure 6A:
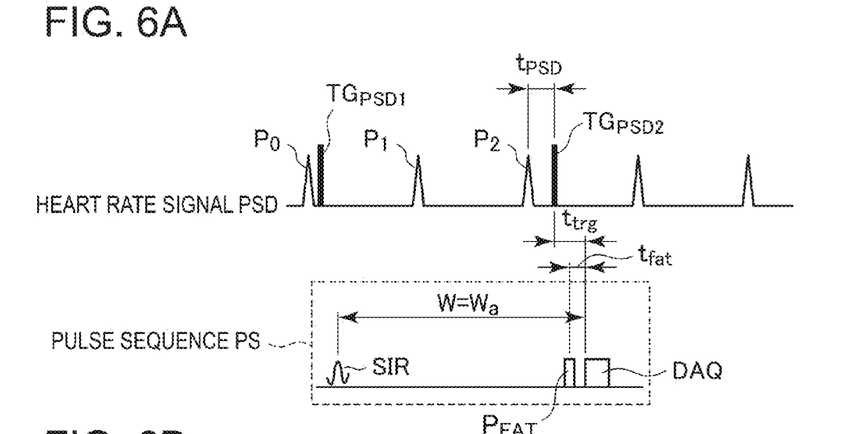
FIGS. 6A and 6B are drawings showing the relation between a heart rate signal PSD and a pulse sequence PS.
Figure 6B:
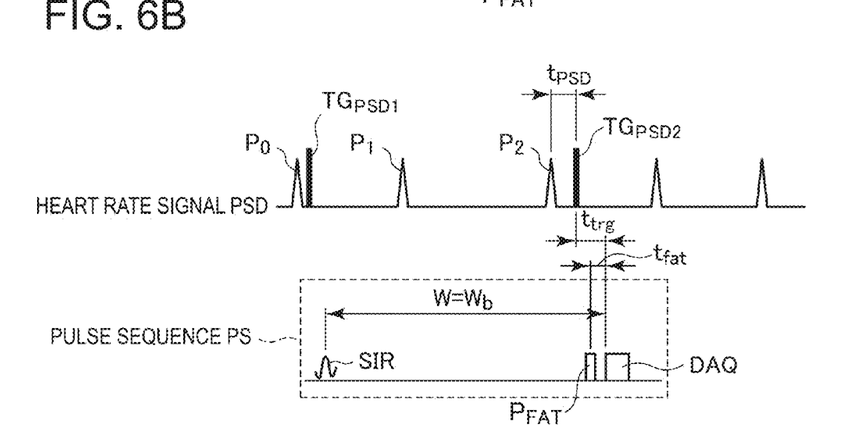

FIGS. 6A and 6B are drawings showing the relation between the heart rate signal PSD and the pulse sequence PS.

FIG. 6A is a drawing showing a pulse sequence PS in a case where the heart rate cycle is regular and FIG. 6B is a drawing showing a pulse sequence PS in a case where the heart rate cycle becomes irregular due to arrhythmia or the like.

First, FIG. 6A will be described.

The trigger generation unit 9 detects a peak of the heart rate signal PSD based on the signal value of the heart rate signal PSD. When the trigger generation unit 9 detects the peak $P_0$, it generates a first heart rate synchronization trigger $TG_{PSD1}$ for transmitting the selective inversion pulse SIR. The first heart rate synchronization trigger $TG_{PSD1}$ may be generated at the position of the peak $P_0$ or may be generated temporally behind the peak $P_0$. In the second embodiment, the first heart rate synchronization trigger $TG_{PSD1}$ is generated temporally behind the peak $P_0$.

When the first heart rate synchronization trigger $TG_{PSD1}$ is generated, the selective inversion pulse SIR is transmitted in synchronization with the first heart rate synchronization trigger $TG_{PSD1}$. The longitudinal magnetization of tissue contained in the inverted region $R_{SIR}$ (Refer to FIG. 2A) is inverted by the selective inversion pulse SIR.

When the trigger generation unit 9 detects a peak $P_2$ of the heart rate signal PSD generated for the second time after the transmission of the selective inversion pulse SIR, when a heart rate delay time $t_{PSD}$ has passed after the detected peak $P_2$, it generates a second heart rate synchronization trigger $TG_{PSD2}$. The second heart rate synchronization trigger $TG_{PSD2}$ is a trigger for carrying out the data acquisition sequence DAQ during diastole.

When the second heart rate synchronization trigger $TG_{PSD2}$ is generated, the fat suppression pulse $P_{FAT}$ is transmitted and the data acquisition sequence DAQ is carried out. In FIG. 6A, the time interval from the second heart rate synchronization trigger $TG_{PSD2}$ to when the data acquisition sequence DAQ is started is indicated by symbol "$t_{trg}$", and the time interval from the fat suppression pulse $P_{FAT}$ to when the data acquisition sequence DAQ is started is indicated by symbol "$t_{fat}$."

The time interval $t_{trg}$ from the second heart rate synchronization trigger $TG_{PSD2}$ to when the data acquisition sequence DAQ is started takes a value so set that the data acquisition sequence DAQ can be carried out during diastole. A fixed value determined before the subject 14 is scanned can be taken for the time interval $t_{trg}$. However, the heart rate cycle of the subject 14 may be measured periodically (for example, at intervals of several seconds to several tens of seconds) while the subject 14 is scanned, and the value of time interval $t_{trg}$ may be changed based on the latest measured heart rate cycle. The time interval $t_{fat}$ from the fat suppression pulse $P_{FAT}$ to when the data acquisition sequence DAQ is started generally has a fixed value. However, the value may be changed as required.

FIG. 6B shows an example in which the interval between peaks P1 and P2 of the heart rate signal PSD becomes wider than in FIG. 6A due to arrhythmia or the like while the subject 14 is scanned. Also in FIG. 6B, the pulse sequence PS is carried out in the same manner as in FIG. 6A and accordingly, detailed description of FIG. 6B will be omitted.

In the second embodiment, a peak $P_2$ that occurs after the transmission of the selective inversion pulse SIR is detected and a second heart rate synchronization trigger $TG_{PSD2}$ is generated behind the peak $P_2$ by a heart rate delay time $t_{PSD}$. Therefore, even though the heart rate cycle of the subject 14 is instantaneously changed by arrhythmia or the like during scanning, the generation timing of the second heart rate synchronization trigger $TG_{PSD2}$ is changed in accordance with this change. Therefore, the value of wait time W of the pulse sequence PS is also changed. As is apparent from the comparison of FIG. 6A and FIG. 6B, the wait time W of the pulse sequence PS is $W=W_a$ in FIG. 6A while the wait time W of the pulse sequence PS is changed to $W=W_b$ in FIG. 6B. Therefore, the start timing of the data acquisition sequence DAQ can be adjusted by taking a variable value for the wait time W. This makes it possible to carry out the data acquisition sequence DAQ during diastole even though arrhythmia occurs during scanning and obtain an image with enhanced arterial blood.

Also in the second embodiment, the wait time W of the pulse sequence PS varies during scanning as in the first embodiment. However, as described with reference to the simulation result shown in FIGS. 4A-4C, it is guessed that any variation in the wait time W of the pulse sequence PS has relatively little influence on image quality.

Third Embodiment

In the description of the third embodiment, a case where both the respiratory gating method and the heart rate gating method are used to acquire an image of a subject will be taken as an example.

Figure 7:
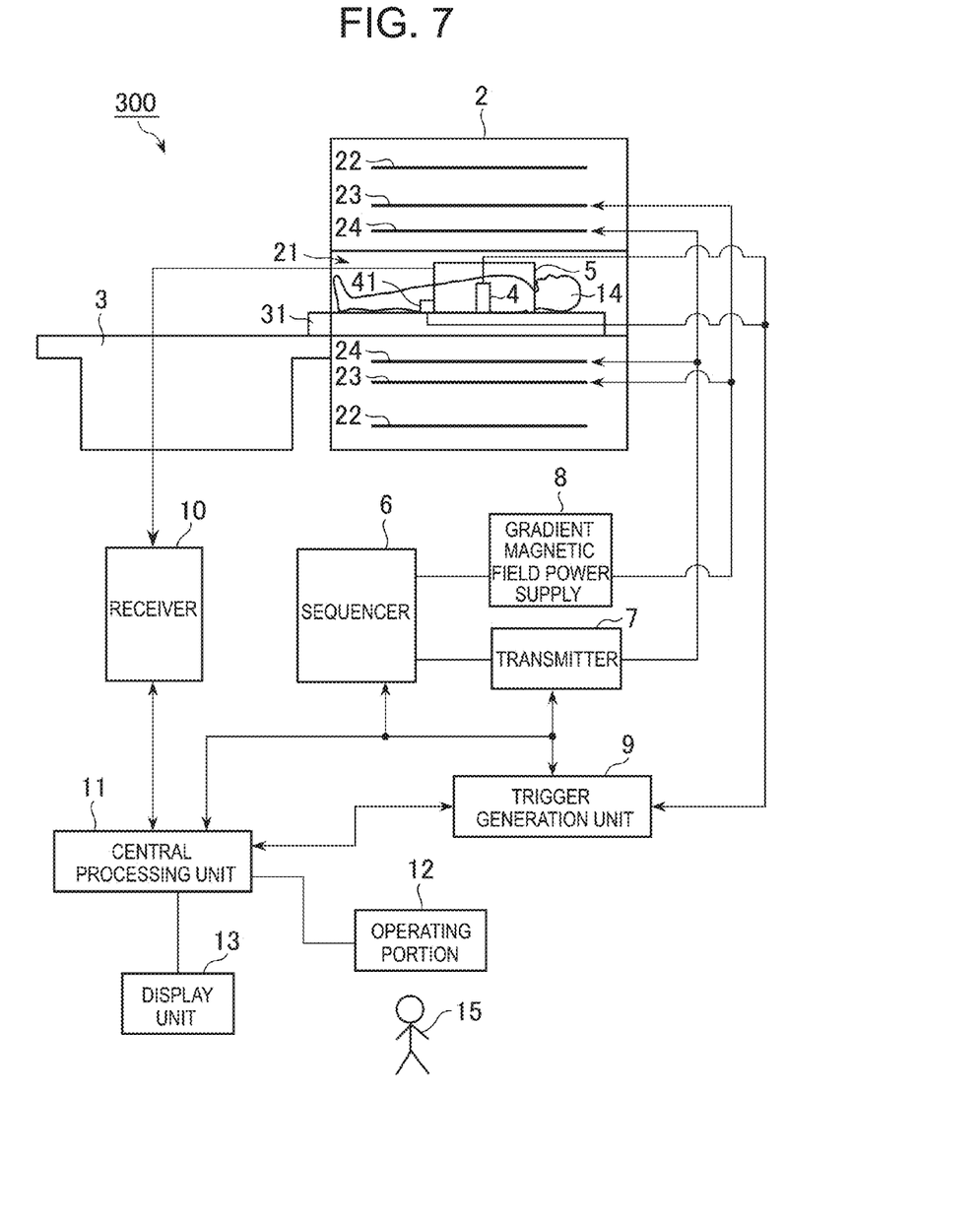
FIG. 7 is a diagram showing an MRI apparatus in a third embodiment.

FIG. 7 is a diagram showing an MRI apparatus 300 in the third embodiment.

The MRI apparatus 300 in the third embodiment is different from the MRI apparatus 100 in the first embodiment in that a heart rate sensor 41 for acquiring heart rate signals from the subject 14 is provided in addition to the bellows 4. The heart rate sensor 41 is, for example, a sphygmograph sensor. The third embodiment is also different in that trigger generation unit 9 generates a respiration synchronization trigger based on a respiration signal from the bellows 4 and generates a heart rate synchronization trigger based on a heart rate signal from the heart rate sensor 41.

The other configuration elements are the same as those of the MRI apparatus 100 in the first embodiment and the description thereof will be omitted.

The MRI apparatus 300 in the third embodiment is configured as mentioned above. Description will be given to a method for scanning the subject 14 in the third embodiment. The image acquisition region R and the pulse sequence PS in the third embodiment are as shown in FIGS. 2A and 2B similarly to the first embodiment.

Figure 8A:
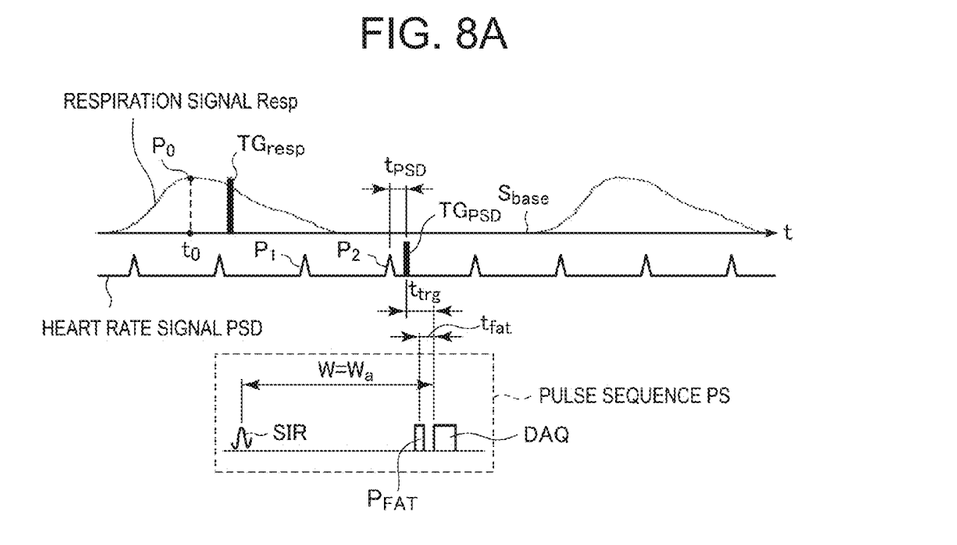
FIGS. 8A and 8B are drawings showing the relation between a respiration signal Resp, a heart rate signal PSD, and a pulse sequence PS in the third embodiment.
Figure 8B:
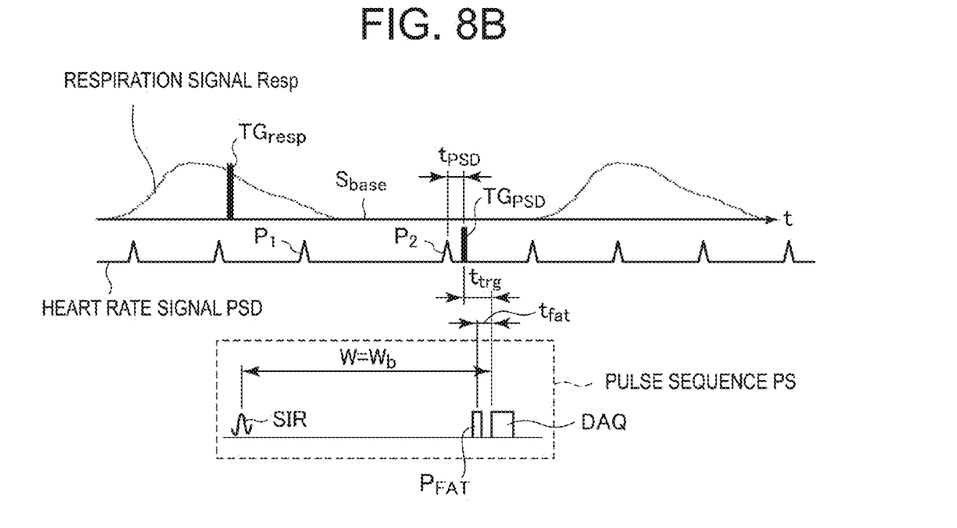

FIGS. 8A and 8B are drawings showing the relation between the respiration signal Resp, the heart rate signal PSD, and the pulse sequence PS in the third embodiment.

FIG. 8A is a drawing showing a pulse sequence PS in a case where the heart rate cycle is regular and FIG. 8B is a drawing showing a pulse sequence PS in a case where the heart rate cycle becomes irregular due to arrhythmia or the like.

First, FIG. 8A will be described.

The trigger generation unit 9 detects a peak of the respiration signal Resp based on the signal value of the respiration signal Resp. In FIG. 8A, the peak $P_0$ of the respiration signal Resp occurs at time $t_0$. Therefore, the trigger generation unit 9 detects the peak $P_0$. When the trigger generation unit 9 detects the peak $P_0$, it generates a respiration synchronization trigger $TG_{resp}$ for transmitting the selective inversion pulse SIR. The respiration synchronization trigger $TG_{resp}$ may be generated at the position of the peak $P_0$ or may be generated temporally behind the peak $P_0$. In the third embodiment, the respiration synchronization trigger $TG_{resp}$ is generated temporally behind the peak $P_0$.

When the respiration synchronization trigger $TG_{resp}$ is generated, the selective inversion pulse SIR is transmitted in synchronization with the respiration synchronization trigger $TG_{resp}$. The longitudinal magnetization of tissue contained in the inverted region $R_{SIR}$ (Refer to FIG. 2A) is inverted by the selective inversion pulse SIR.

When the trigger generation unit 9 detects a peak $P_2$ of the heart rate signal PSD generated for the second time after the transmission of the selective inversion pulse SIR, when a heart rate delay time $t_{PSD}$ has passed after the detected peak $P_2$, it generates a heart rate synchronization trigger $TG_{PSD}$. The heart rate synchronization trigger $TG_{PSD}$ is a trigger for carrying out the data acquisition sequence DAQ during diastole.

When the heart rate synchronization trigger $TG_{PSD}$ is generated, the fat suppression pulse $P_{FAT}$ is transmitted and the data acquisition sequence DAQ is carried out. In FIG. 8A, the time interval from the heart rate synchronization trigger $TG_{PSD}$ to when the data acquisition sequence DAQ is started is indicated by symbol "$t_{trg}$", and the time interval from the fat suppression pulse $P_{FAT}$ to when the data acquisition sequence DAQ is started is indicated by symbol "$t_{fat}$."

The time interval $t_{trg}$ from the heart rate synchronization trigger $TG_{PSD}$ to when the data acquisition sequence DAQ is started is set so that the data acquisition sequence DAQ can be carried out during diastole. A fixed value determined before the subject 14 is scanned can be taken for the time interval $t_{trg}$. However, the heart rate cycle of the subject 14 may be measured periodically (for example, at intervals of several seconds to several tens of seconds) while the subject 14 is scanned, and the value of time interval $t_{trg}$ may be changed based on the latest measured heart rate cycle. The time interval $t_{fat}$ from the fat suppression pulse $P_{FAT}$ to when the data acquisition sequence DAQ is started generally has a fixed value; however, the value may be changed as required.

FIG. 8B shows an example in which the interval between peaks $P_1$ and $P_2$ of the heart rate signal PSD becomes wider than in FIG. 8A due to arrhythmia or the like while the subject 14 is scanned. Also in FIG. 8B, the pulse sequence PS is carried out in the same manner as in FIG. 8A and accordingly, detailed description of FIG. 8B will be omitted.

In the third embodiment, a peak $P_2$ that occurs after the transmission of the selective inversion pulse SIR is detected. Then the heart rate synchronization trigger $TG_{PSD}$ for carrying out the data acquisition sequence DAQ is generated behind the peak $P_2$ by a heart rate delay time $t_{PSD}$. Therefore, if the heart rate cycle of the subject 14 is instantaneously changed by arrhythmia or the like during scanning, the generation timing of the heart rate synchronization trigger $TG_{PSD}$ is changed in accordance with this change. As a result, the value of wait time W of the pulse sequence PS is also changed. As is apparent from the comparison of the FIG. 8A and FIG. 8B, the wait time W of the pulse sequence PS is $W=W_a$ in FIG. 8A while the wait time W of the pulse sequence PS is changed to $W=W_b$ in FIG. 8B. Therefore, the start timing of the data acquisition sequence DAQ can be adjusted by taking a variable value for the wait time W. This makes it possible to carry out the data acquisition sequence DAQ during diastole even though arrhythmia occurs during scanning and obtain an image with enhanced arterial blood.

Also in the third embodiment, the wait time W of the pulse sequence PS varies during scanning as in the first embodiment. However, as described with reference to the simulation result in FIGS. 4A-4C, it is guessed that it has relatively little influence on image quality.

Fourth Embodiment

In the description of the fourth embodiment, another case where both the respiratory gating method and the heart rate gating method are used to acquire an image of a subject will be taken as an example.

An MRI apparatus in the fourth embodiment is different from the MRI apparatus 300 in the third embodiment in that two respiration synchronization triggers are generated. The other configuration elements are the same as those of the MRI apparatus 300 in the third embodiment and the description thereof will be omitted.

Description will be given to a method for scanning the subject 14 in the fourth embodiment with reference to FIGS. 9A and 9B.

Figure 9A:
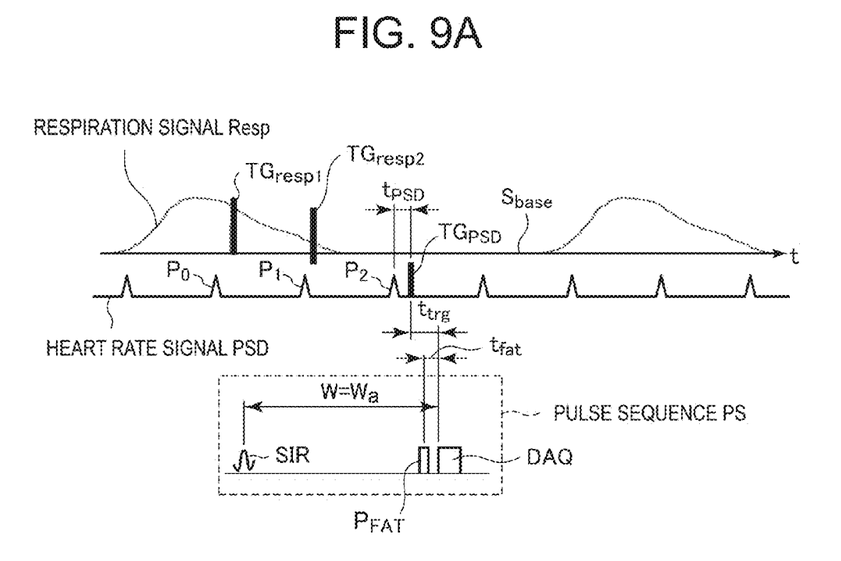
FIGS. 9A and 9B are drawings showing the relation between a respiration signal Resp, a heart rate signal PSD, and a pulse sequence PS in a fourth embodiment.
Figure 9B:
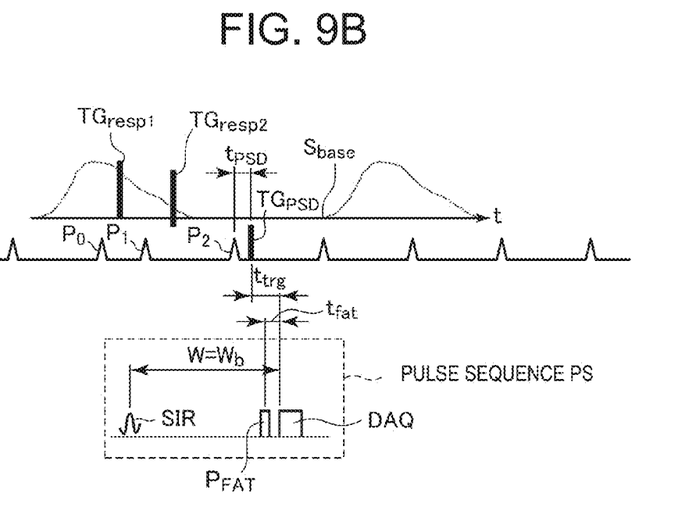

FIGS. 9A and 9B are drawings showing the relation between the respiration signal Resp, the heart rate signal PSD, and the pulse sequence PS in the fourth embodiment.

FIG. 9A is a drawing showing a pulse sequence PS in the case of heart rate cycle $T_a$, and FIG. 9B is a drawing showing a pulse sequence PS in a case where the heart rate cycle changes from $T_a$ to $T_b$ and the heart rate cycle becomes irregular due to arrhythmia or the like.

First, FIG. 9A will be described.

In the fourth embodiment, a first respiration synchronization trigger $TG_{resp1}$ and a second respiration synchronization trigger $TG_{resp2}$ are generated based on the respiration signal Resp. The first respiration synchronization trigger $TG_{resp1}$ and the second respiration synchronization trigger $TG_{resp2}$ are generated in the same manner as in the first embodiment.

The trigger generation unit 9 detects a peak $P_2$ of the heart rate signal PSD that occurs for the first time after the generation of the second respiration synchronization trigger $TG_{resp2}$. When the peak $P_2$ of the heart rate signal PSD is detected, a heart rate synchronization trigger $TG_{PSD}$ is generated when a heart rate delay time $t_{PSD}$ has passed after the detected peak $P_2$. The heart rate synchronization trigger $TG_{PSD}$ is a trigger for carrying out the data acquisition sequence DAQ during diastole.

When the heart rate synchronization trigger $TG_{PSD}$ is generated, the fat suppression pulse $P_{FAT}$ is transmitted and the data acquisition sequence DAQ is carried out. In FIG. 9A, the time interval from the heart rate synchronization trigger $TG_{PSD}$ to when the data acquisition sequence DAQ is started is indicated by symbol "$t_{trg}$", and the time interval from the fat suppression pulse $P_{FAT}$ to when the data acquisition sequence DAQ is started is indicated by symbol "$t_{fat}$."

The time interval $t_{trg}$ from the heart rate synchronization trigger $TG_{PSD}$ to when the data acquisition sequence DAQ is started takes a value so set that the data acquisition sequence DAQ can be carried out during diastole. A fixed value determined before the subject 14 is scanned can be taken for the time interval $t_{trg}$. However, the heart rate cycle of the subject 14 may be measured periodically (for example, at intervals of several seconds to several tens of seconds) while the subject 14 is scanned, and the value of time interval $t_{trg}$ may be changed based on the latest measured heart rate cycle. The time interval $t_{fat}$ from the fat suppression pulse $P_{FAT}$ to when the data acquisition sequence DAQ is started generally has a fixed value; however, the value may be changed as required.

FIG. 9B shows an example in which the respiratory cycle of the subject is changed from $T_a$ to $T_b$ and the interval between peaks $P_0$ and $P_1$ of the heart rate signal PSD becomes narrower than in FIG. 9A due to arrhythmia or the like. Also in FIG. 9B, the pulse sequence PS is carried out in the same manner as in FIG. 9A and accordingly, detailed description of FIG. 9B will be omitted.

In the fourth embodiment, the second respiration synchronization trigger $TG_{resp2}$ is generated when after the selective inversion pulse SIR is transmitted, the respiration signal Resp gets close to the base line $S_{base}$. Therefore, if the respiratory cycle of the subject 14 changes during scanning, the generation timing of the second respiration synchronization trigger $TG_{resp2}$ is changed in accordance with this change. As a result, the value of the wait time W of the pulse sequence PS is also changed. As is apparent from the comparison of FIG. 9A and FIG. 9B, the wait time W of the pulse sequence PS is $W=W_a$ in FIG. 9A while the wait time W of the pulse sequence PS is changed to $W=W_b$ in FIG. 9B. Therefore, the start timing of the data acquisition sequence DAQ can be adjusted by taking a variable value for the wait time W. This makes it possible to carry out the data acquisition sequence DAQ while the body motion of the subject 14 arising from respiration is small and obtain an image with reduced body motion artifacts.

In the fourth embodiment, further, a peak $P_2$ of the heart rate signal PSD that occurs for the first time after the generation of the second respiration synchronization trigger $TG_{resp2}$ is detected, and a heart rate synchronization trigger $TG_{PSD}$ is generated behind this peak $P_2$ by a heart rate delay time $t_{PSD}$. Therefore, if the heart rate cycle of the subject 14 is instantaneously changed by arrhythmia or the like during scanning, the generation timing of the heart rate synchronization trigger $TG_{PSD}$ is changed in accordance with this change. As a result, the value of wait time W of the pulse sequence PS is changed. For this reason, the start timing of the data acquisition sequence DAQ can be adjusted by taking a variable value for the wait time W. This makes it possible to carrying the data acquisition sequence DAQ during diastole even though arrhythmia occurs during scanning and obtain an image with enhanced arterial blood.

Also in the fourth embodiment, the wait time W of the pulse sequence PS varies during scanning as in the first embodiment. However, as described with reference to the simulation result in FIGS. 4A-4C, it is guessed that it has relatively little influence on image quality.

Many widely different embodiments may be configured without departing from the spirit and the scope of the present invention. It should be understood that the present invention is not limited to the specific embodiments described in the specification, except as defined in the appended claims.

The invention claimed is:

1. A magnetic resonance imaging apparatus configured to carry out a pulse sequence in synchronization with a biosignal,
   wherein the pulse sequence includes:
      an RF pulse; and
      a data acquisition sequence for acquiring data when a wait time has passed after the RF pulse;
   the magnetic resonance imaging apparatus comprising a trigger generation unit configured to generate a trigger for carrying out the pulse sequence based on the biosignal, wherein the biosignal includes a respiration signal and a heart rate signal, and wherein the trigger generation unit is configured to generate, based on the respiration signal, a first respiration synchronization trigger for transmitting the RF pulse and, after the RF pulse is transmitted, a second respiration synchronization trigger for carrying out the data acquisition sequence while the body motion of a subject due to respiration is small, the trigger generation unit further configured to generate, based on the heart rate signal and after the second respiration synchronization trigger is generated, a heart rate synchronization trigger for carrying out the data acquisition sequence during diastole.

2. The magnetic resonance imaging apparatus according to claim 1, wherein the pulse sequence includes a fat suppression pulse configured to suppress fat.

3. A magnetic resonance imaging method for carrying out a pulse sequence in synchronization with a biosignal that includes a respiration signal and a heart rate signal, the method comprising:
   transmitting an RF pulse;
   acquiring data in a data acquisition sequence when a wait time has passed after the RF pulse;
   generating a first respiration synchronization trigger, based on the respiration signal, for transmitting the RF pulse,
   after the RF pulse is transmitted:
      generating a second respiration synchronization trigger, based on the respiration signal, for carrying out the data acquisition sequence while the body motion of a subject undergoing magnetic resonance imaging due to respiration is small; and
      generating a heart rate synchronization trigger, based on the heart rate signal and generated after the second respiration synchronization trigger is generated, for carrying out the data acquisition sequence during diastole.

4. The magnetic resonance imaging method according to claim 3, wherein the pulse sequence includes a fat suppression pulse configured to suppress fat.

5. A magnetic resonance imaging apparatus configured to carry out a pulse sequence in synchronization with a biosignal,
   wherein the pulse sequence includes:
      an RF pulse; and
      a data acquisition sequence for acquiring data when a wait time has passed after the RF pulse;
   the magnetic resonance imaging apparatus comprising a trigger generation unit configured to generate a trigger for carrying out the pulse sequence based on the biosignal, wherein the biosignal includes a respiration signal and a heart rate signal, and wherein the trigger generation unit is configured to generate, based on the respiration signal, a first respiration synchronization trigger for transmitting the RF pulse and, after the RF pulse is transmitted, a second respiration synchronization trigger for carrying out the data acquisition sequence while the body motion of a subject due to respiration is small, the trigger generation unit further configured to generate, based on the heart rate signal and after the second respiration synchronization trigger is generated, a heart rate synchronization trigger for carrying out the data acquisition sequence during diastole.

6. The magnetic resonance imaging apparatus according to claim 5, wherein the pulse sequence includes a fat suppression pulse configured to suppress fat.

7. The magnetic resonance imaging apparatus according to claim 2, wherein the fat suppression pulse is transmitted between the RF pulse and the data acquisition sequence.

8. The magnetic resonance imaging method according to claim 4, wherein the fat suppression pulse is transmitted between the RF pulse and the data acquisition sequence.

9. The magnetic resonance imaging apparatus according claim 1, wherein the wait time is determined based on the heart rate signal.

10. The magnetic resonance imaging method according to claim 3, wherein the wait time is determined based on the heart rate signal.

* * * * *